United States Patent [19]
Shultz

[11] Patent Number: 5,326,886
[45] Date of Patent: Jul. 5, 1994

[54] MAINTAINING VPO CATALYST PERFORMANCE BY ALUMINIZING REACTOR INTERNALS IN OXIDATION OF BUTANE TO MALEIC ANHYDRIDE

[75] Inventor: John T. Shultz, Medina, Ohio

[73] Assignee: The Standard Oil Company, Cleveland, Ohio

[21] Appl. No.: 803,947

[22] Filed: Dec. 9, 1991

[51] Int. Cl.$^5$ .............................................. C07D 307/60
[52] U.S. Cl. .................................... 549/259; 599/258; 599/260; 422/241
[58] Field of Search ................ 549/259, 258; 422/240, 422/241

[56] References Cited

U.S. PATENT DOCUMENTS

| | | | |
|---|---|---|---|
| 1,854,882 | 4/1932 | Calcott et al. | 549/248 |
| 1,872,956 | 8/1932 | Jaeger et al. | 549/248 |
| 3,353,923 | 11/1967 | Peters | 549/248 |

FOREIGN PATENT DOCUMENTS

| | | |
|---|---|---|
| 5936909 | 8/1977 | Japan . |
| 54-046712 | 4/1979 | Japan . |
| 54-046713 | 4/1979 | Japan . |
| 89318823 | 8/1991 | Japan . |
| 644637 | 8/1984 | Switzerland . |

*Primary Examiner*—Bernard Dentz
*Attorney, Agent, or Firm*—David P. Yusko; Michael F. Esposito; David J. Untener

[57] ABSTRACT

Catalysts comprising a compound of vanadium, phosphorus and oxygen which are employed in the oxidation of n-butane to maleic anhydride are protected from contamination caused by side reactions which occur between the catalyst and steel process equipment by covering the process equipment surfaces which contact the catalyst at elevated temperatures with a coating comprising aluminum oxide.

15 Claims, No Drawings

MAINTAINING VPO CATALYST PERFORMANCE BY ALUMINIZING REACTOR INTERNALS IN OXIDATION OF BUTANE TO MALEIC ANHYDRIDE

BACKGROUND OF THE INVENTION

1. Field of the Invention

This invention relates to the use of aluminum oxide ($Al_2O_3$) as a coating for reactor internals. Specifically, it has been discovered that the internals of metallic reactors and other metallic chemical process components (i.e., piping, cyclones) which are exposed to catalyst utilized in various chemical processes, react with the catalyst to form compounds which eventually coat the catalyst causing a loss of catalytic activity or otherwise inhibiting catalyst performance. In particular this invention relates to coating with aluminum oxide reactor internals for processes for the oxidation of n-butane to maleic anhydride which utilize a catalyst comprising a compound of vanadium, phosphorus and oxygen.

2. Description of the Prior Art

Reactor vessels and associated hardware and piping used in refinery and chemical processes are typically constructed of carbon or low alloy steel. Where corrosion is a problem, stainless steel or other corrosion resistant materials including aluminum oxide are employed.

A focus of the instant invention are catalytic processes for the oxidation of hydrocarbons which utilize catalysts comprising a compound of vanadium, phosphorus and oxygen and which operate at elevated temperatures. Typically, the reactors for these processes have been fabricated from carbon or low alloy steel. It has been discovered that steel surfaces exposed to such catalyst at elevated temperatures react with the catalyst to produce contaminants which coat the exterior of the catalyst thereby inhibiting catalyst performance. This problem becomes particularly troublesome in fluid bed reactors where catalyst particles are continually circulating as the catalyst particles are suspended in a stream of upward flowing gases, and where contaminants are easily commingled with the catalyst and the circulating catalyst has numerous opportunities to contact metallic surfaces.

The above phenomena and the ill effects caused thereby have been detected in fluid bed processes for the catalytic oxidation of n-butane to maleic anhydride. In this process the catalyst comprising a compound of vanadium, phosphorus and oxygen and operating in carbon or low alloy steel (including stainless steel) reactors eventually acquire iron containing contaminants on the catalyst surface which causes a loss of catalyst activity as well as a loss in catalyst fluidization quality.

An object of this invention is a means to eliminate the production of such contaminants in processes for the catalytic oxidation of n-butane to maleic anhydride thereby maintaining the activity and performance of the catalyst used therein.

SUMMARY OF THE INVENTION

The invention relates to a process for the oxidation of hydrocarbons, preferably the oxidation of n-butane to maleic anhydride, wherein the process utilizes a catalyst comprising a compound of vanadium, phosphorus and oxygen and wherein the reactor inner shell surface, cooling coils, cyclones, piping, and other metallic surfaces which come into contact with the catalyst at elevated temperatures are coated with aluminum oxide.

In one embodiment, the invention relates to a metallic reaction vessel for use in the oxidation of hydrocarbons in the presence of catalyst comprising phosphorus, wherein the reaction vessel internals are covered with a coating comprising aluminum oxide.

In yet another embodiment, the invention relates to a method of preventing contamination of the catalyst comprising phosphorus and used in a chemical process for the oxidation of hydrocarbons, wherein the method comprises covering the metallic surfaces of process equipment which may come into contact with the catalyst at elevated temperatures with a coating comprising aluminum oxide.

DETAILED DESCRIPTION OF THE INVENTION

Maleic anhydride is produced by the oxidation of n-butane in a fluid bed reactor in the presence of a fluid bed catalyst comprising a compound of vanadium, phosphorus and oxygen, usually the catalyst is an oxide of vanadium and phosphorus. These processes operate at elevated reactor temperatures in excess of 400° C. After several months of operation, a decrease in the catalyst activity and fluidization quality is experienced. This has been attributed to the contamination of the fluid bed catalyst particles with iron containing components. Not only is the contaminated catalyst less catalytically active for the oxidation of n-butane to maleic anhydride, but the contamination is somewhat "sticky" causing the fluid bed catalyst particles to agglomerate into larger particles which become too heavy to remain suspended in the upward rising reaction gases (i.e., the catalyst has lost fluidization quality).

While not intending to be bound by theory, it is theorized that the catalyst reacts with the reactor and other metallic surfaces to produce a contaminant which ultimately coats the catalyst surface. Specifically a catalyst comprising an oxide of vanadium and phosphorus will contain some $P_2O_5$. At elevated temperatures (about and greater than 200° C.) the catalyst will react with oxides of iron, nickel or chromium (at least one of which is common to all commercial grades of steel) to change the valence of the vanadium and release $P_2O_5$ and possibly $PO_2$ as a vapor. One or both of these vapors react with metallic iron or iron oxides common to the reaction vessel or piping surfaces to form an oxide of iron and phosphorus. In many respects, this oxide of iron and phosphorus resembles a glass and on occasion shall be referred to hereinafter as the "glass". The oxide of iron and phosphorus coats everything in the system (e.g. reactor walls, cooling coils, piping, etc.). As the oxide of iron and phosphorus becomes more mature, it also absorbs vanadium and vanadium oxides from the catalyst and becomes brittle. Given either or both events of (i) the brittle glass reaching critical thickness or (ii) the brittle glass having a different thermal coefficient of expansion than the metallic substrate on which it formed when combined with the thermal cycling (temperature variations) of the reactor or its components, the now mature and brittle glass spalls (breaks or chips into small fragments) randomly from the glass coated surfaces. These spalled glass fragments become attritted to ever smaller particles in the turbulence of fluidization and by violent contact with the reactor components. The ever smaller particles soon become attached to the reactor components where the glass is not yet mature and to individual catalyst particles. As the catalyst particles become coated with even smaller particles of oxides of iron, phosphorus, and vanadium and the latter oxide particles dissolve into the catalyst surface, the catalyst particles become "sticky" and begin to agglomerate and the porosity of the catalyst is diminished. As such, the optimal catalytic surface is less likely to contact the reactants. All of this leads to a drop in conversion of the reactants to the preferred product.

A solution to this problem has been discovered. Specifically, all carbon and low alloy steel (including stainless steel) surfaces inside the process which are exposed to the catalyst at elevated temperatures are coated or otherwise shielded with aluminum oxide (alpha-$Al_2O_3$). It has been discovered that the aluminum oxide prevents the reaction which occurs between the catalyst and the metal surfaces. The result is a catalyst which maintains its fluidization quality and a high level of conversion because its surface is no longer inundated with contaminants.

The various metal surfaces found inside the process can be coated by aluminum oxide by any suitable method. Representative methods include block or cast refractory (where the aluminum oxide is cast in the form of bricks and may be bonded together to add stability or where it may be cast directly onto the steel surface given suitable support), diffused coatings (where the steel is covered with aluminum and aluminum oxide powder which is subsequently "baked" into the metal surface); and plasma jet sprayed coatings. The goal of any coating method is to prevent contact between the catalyst particles and the steel process equipment surfaces.

Typically, different surfaces inside the process require different coating techniques. For example, the reactor vessel air grid and reactor effluent lines are coated by refractory; and the cooling coils, the cyclones, and the feed spargers receive the baked aluminum oxide coating. Seams between components are sealed by plasma jet coating, ion jet coating, electron beam coating or equivalent coating techniques.

The thickness of the aluminum oxide coating is not critical, as long as the metal surfaces are adequately sealed from contacting the catalyst particles. Often the coating method will determine the thickness of the aluminum oxide coating. For example, the thickness of the refractory coating would likely be measured in inches, while the thickness of the sprayed coatings would be measured in one or more thousandths of an inch or fraction thereof.

In coating the internal metal process surfaces alpha-$Al_2O_3$ is to be employed because of its inherent inertness. Beta-$Al_2O_3$ and gamma-$Al_2O_3$ are chemically active and should be avoided. Any inert material capable of withstanding the elevated reaction temperatures are equivalents to the aluminum oxide coating and suitable for use in this invention. A suitable substitute for the aluminum oxide is silicon oxide which may be used in place of or in combination with the aluminum oxide.

The instant invention has been described in terms of its applicability and benefits for a fluid bed process for the oxidation of $n$-butane to maleic anhydride utilizing a catalyst comprising vanadium, phosphorus and oxygen. Specifically, the coating of the process equipment internals prevents the side reactions which occur between the metal surfaces and catalyst to form the contaminants which coat the catalyst causing a loss in catalyst activity and fluidization quality. However, the instant invention is applicable to any chemical or refining process both fixed and fluid bed which utilize a phosphorus containing catalyst inside steel process equipment. In such processes the reaction temperature may vary widely and is dependent upon the particular hydrocarbon and catalyst employed. Normally in such processes temperatures of up to about 600° C. are employed. For the fluid catalytic bed oxidation of $n$-butane to maleic anhydride utilizing a catalyst comprising an oxide of vanadium and phosphorus reaction temperatures of about 325° C. to about 500° C. are more typical. Associated process equipment and piping which come into contact with the catalyst will have temperatures as low as 200° C.

The foregoing description of the present invention have been presented for the purpose of illustration. This description is not intended to be exhaustive or to limit the invention to the precise form disclosed, and obviously many modifications and variations are possible in light of the above disclosure. The foregoing description attempts to best explain the principle of the invention and its practical applications and to thereby enable others skilled in the art to best utilize the invention in its various embodiments and with various modifications as are suited to the particular use contemplated. It is intended that the invention be defined by the following claims.

The claimed invention is:

1. A fluid-bed process for the oxidation of $n$-butane to produce maleic anhydride wherein said process utilizes a catalyst comprising phosphorus, wherein metallic surfaces of process equipment which come into contact with the catalyst at elevated temperatures are covered with a coating comprising aluminum oxide.

2. The process of claim 1 wherein the catalyst comprises a compound of vanadium, phosphorus and oxygen.

3. The process of claim 1 wherein the elevated temperature is between about 200° to about 600° C.

4. The process of claim 1 wherein the aluminum oxide is alpha-$Al_2O_3$.

5. The process of claim 1 wherein the coating comprising aluminum oxide is at least one of cast refractory coating, block refractory coating, diffused coating, plasma jet spray coating, ion jet coating or electron beam coating.

6. The process of claim 1 wherein the process equipment comprises at least one of the reactor, cooling coil, cyclone and process piping.

7. The process of claim 1 wherein the coating comprises aluminum oxide and silicon oxide.

8. A method for preventing contamination of a catalyst comprising phosphorus and employed in a fluid-bed chemical process for the oxidation of $n$-butane to produce maleic anhydride, wherein the method comprises covering the internal metallic surfaces of the process equipment which come into contact with the catalyst at elevated temperatures with a coating comprising aluminum oxide.

9. The method of claim 8 wherein the catalyst comprises a compound of vanadium, phosphorus and oxygen.

10. The method of claim 8 wherein the elevated temperature is between about 200° to about 600° C.

11. The method of claim 8 wherein the aluminum oxide is alpha-$Al_2O_3$.

12. The method of claim 8 wherein the coating comprising aluminum oxide is at least one of cast refractory coating, block refractory coating, diffused coating, plasma jet spray coating, ion Jet coating or electron beam coating.

13. The method of claim 8 wherein the process equipment comprises at least one of the reactor, cooling coil, cyclone and process piping.

14. The method of claim 8 wherein the coating comprises aluminum oxide and silicon oxide.

15. A method for preventing contamination of a catalyst comprising a compound of vanadium, phosphorus, and oxygen and employed in a fluid-bed process for the oxidation of $n$-butane to maleic anhydride, said contamination caused by a chemical reaction at elevated temperatures between components in the catalyst and the steel used in the construction of process equipment, said method comprising covering the steel surfaces of the process equipment which comes into contact with the catalyst at elevated temperatures with a coating comprising aluminum oxide.

* * * * *